: US 7,689,320 B2
(45) Date of Patent: Mar. 30, 2010

(12) United States Patent
Prisco et al.

(54) ROBOTIC SURGICAL SYSTEM WITH JOINT MOTION CONTROLLER ADAPTED TO REDUCE INSTRUMENT TIP VIBRATIONS

(75) Inventors: Giuseppe Prisco, Mountain View, CA (US); David J. Rosa, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 762 days.

(21) Appl. No.: 11/509,172

(22) Filed: Aug. 24, 2006

(65) Prior Publication Data
US 2007/0142968 A1 Jun. 21, 2007

Related U.S. Application Data

(60) Provisional application No. 60/751,947, filed on Dec. 20, 2005.

(51) Int. Cl.
*G06F 19/00* (2006.01)
(52) U.S. Cl. .................. 700/245; 700/264; 318/568.11; 318/568.12
(58) Field of Classification Search .................. 700/245, 700/264
See application file for complete search history.

(56) References Cited

U.S. PATENT DOCUMENTS

| 4,068,156 | A | * | 1/1978 | Johnson et al. ............. 318/575 |
| 4,883,400 | A | * | 11/1989 | Kuban et al. .................... 414/2 |
| 5,252,901 | A | * | 10/1993 | Ozawa et al. ........... 318/568.12 |
| 6,364,888 | B1 | | 4/2002 | Niemeyer et al. |
| 2002/0112855 | A1 | * | 8/2002 | Arndt et al. ............. 166/250.15 |
| 2002/0159606 | A1 | * | 10/2002 | Hobelsberger ................ 381/96 |
| 2003/0004610 | A1 | * | 1/2003 | Niemeyer et al. ........... 700/245 |
| 2003/0018400 | A1 | * | 1/2003 | Tuttle et al. ..................... 700/29 |
| 2004/0128030 | A1 | * | 7/2004 | Nagata et al. ................ 700/245 |
| 2004/0174770 | A1 | * | 9/2004 | Rees ............................... 367/7 |
| 2004/0238758 | A1 | * | 12/2004 | Antonius Theodorus Dams ....................... 250/491.1 |
| 2005/0021176 | A1 | * | 1/2005 | Takenaka et al. ............. 700/245 |
| 2005/0259348 | A1 | * | 11/2005 | Zhang et al. .............. 360/77.02 |
| 2006/0293791 | A1 | * | 12/2006 | Dariush ....................... 700/245 |
| 2007/0013336 | A1 | * | 1/2007 | Nowlin et al. ........... 318/568.21 |

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

(Continued)

*Primary Examiner*—Khoi Tran
*Assistant Examiner*—Rodney King

(57) ABSTRACT

A robotic surgical system has a robot arm holding an instrument for performing a surgical procedure, and a control system for controlling movement of the arm and its instrument according to user manipulation of a master manipulator. The control system includes a filter in its forward path to attenuate master input commands that may cause instrument tip vibrations, and an inverse filter in a feedback path to the master manipulator configured so as to compensate for delay introduced by the forward path filter. To enhance control, master command and slave joint observers are also inserted in the control system to estimate slave joint position, velocity and acceleration commands using received slave joint position commands and torque feedbacks, and estimate actual slave joint positions, velocities and accelerations using sensed slave joint positions and commanded slave joint motor torques.

25 Claims, 9 Drawing Sheets

OTHER PUBLICATIONS

Y. Yokokohji T. Yoshikawa Bilateral Control of Master-Slave Manipulators for Ideal Kinesthetic Coupling- Formulation and Experiments; IEEE Transaction on Robotics and Automation vol. 10 No. 5 Oct. 1994.

A.Sherman M.C.Cavusoglu, F. Tendick ,Comparison of Teleoperator Control Architectures for Palpation Task; IMCE'00 Symp on Haptic Interfaces for Virtual Environment and Teleoperator Systems; Nov. 5-10; Orlando FL.

J. Funda, R.. Taylor, B. Eldrige, S.Gomory, K. Gruben Constrained Cartesian Motion Control for Teleoperated Surgical Robots IEEE Transacations on Robotics and Automation vol. 12 No. 3 June 1996.

R. Anderson M. Spong ;Bilateral Control of Teleoperators with Time Delay; IEEE Transacton on Automatic Control vol. 34 No. 5 May 1989.

M.C. Cavusoglu, F. Tendik, M. Cohon, S. Sastry ; A Laparoscopic Telesurgical Workstation; IEEEE Tranactions on Robotics and Automation vol. 15 No. 4 Aug. 1999.

F.Tendick, M. C. Cavusoglu, N. Dhruv, A. Sherman ; "Maximazing the Sensation of Compliance in Teleoperative Surgery;" $8^{TH}$ International Symposium on Robotics With Aplications (wac 2000) Jun. 16, 2000.

Bilateral controller Design for Telemanipulation in Soft Environments; M. C. Cavusoglu, A. Sherman, F. Tendick; IEEE International Conference on Robotics and Skutomation(ICRA2001), Seoul, Korea May 21-26, 2001.

Keyvan Hashtrudi-Zaad & Salcudean; Septiuiu; Bilateral Parallel Force/Position Teleopertion Control; Journal of Robotic System vol. 19 Issue 4 pp. 155-167.

S.E. Salcudean, S. Ku, G. Bell ; Performance Measurement in Scaled Teleoperation for Microsurgery Proceedings of the First Joint Conference on Computer Vision, Virtual Reality and Robotics in Medicine and Medial Robotics and Computer-Assisted Surgery ; 789-798; 1997.

K. H. Zaad, S. E. Salcudean ;Transparency in Time-Delayed Systems and the Effect of Local Force Feedback for Transparent Teleoperation; IEEE Transaction on Robotics and Automation vol. 18 No. 1, Feb. 2002.

W.H. Zhu, S.E. Salcudean ;"Teleoperation with Adaptive Motion/Force Control" 1999 IEEE International Conference on Robotics and Automation, May 10-15, 1999, Marriott Hotel, Renaissance Center, Detroit, Michigan, Proceedings. IEEE Robotics and Automation Society 1999, vol. 1, p. 231.

D.W. Repperger ; Active Force Reflection Devices in Teleoperation; IEEE vol. 11, Issue 1, Jan. 1991 pp. 52-56.

Murat Cenk Cavusoglu ; Control of a Telesurgical Workstation University of California, Berkeley Technical Report No. UCB/ERL M97/35 1997.

D. A. Lawrence ;Stability and Transparency in Bilateral Teleoperation IEEE Transaction on Robotics and Automation, vol. 9 No. 5 Oct. 1993.

T. Itoh, K. Kosuge, T. Fukuda ;Human-Machine Cooperative Telemanipulation with Motion and Force Scaling Using Task-Oriented Virtual Tool Dynamics IEEE Transactions on Robotics and Automation vol. 16 No. 5 Oct. 2000.

P. Arcara, C. Melchiorri, S. Stramigioli ;"Intrinsically Passive Control in Bilateral Teleoperation Mimi Systems" Proceedings of the European Control Conference 2001 p. 1180-1185.

S.E. Salcudean, M. Zhu, W. Zhu, K. H. Zaad; Transparent Bilateral Teleoperation under Position and Rate Control, The International Journal of Robotics Research, vol. 19, No. 12, 1185-1202 (2000) DOI: 10.1177/02783640022068020.

W. Zhu, S. E. Salcudean ; Stability Guaranteed Teleoperation: an Adaptive Motion/Force Control Approach IEEE Transactions on vol. 45, Issue 11, Nov. 2000 pp. 1951-1969.

W. H. Zhu, S. E. Salcudean M. Zhu ; Experiments with Transparent Teleoperation under Position and Rate Control;. : *Robotics and Automation, 1999. Proceedings. 1999 IEEE International Conference* ; 1870-1875 vol. 3.

J.H. Ryu, D.S. Kwon, B. Hannaford; Stable Teleoperation with Time Domain Passivity Control "Jee-Hwan Ryu, Dong-Soo Kwon, and Blake Hannaford," Proc. of the 2002 IEEE Int. Conf. on Robotics & Automation, Washington DC, USA, pp. 1863-1869.

J. Rosen, B. Hannaford, M. MacFarlane, M. N. Sinanan ; Force Controlled and Teleoperated Endoscopic Grasper for Minimally Invasive Surgery- Experimental Performance Evaluation; IEEE Transactions on Bimedical Engineering vol. 46, No. 10 Oct. 1999.

P.J. Hacksel, S. E. Salcudean ; "Estimation of Enviroment Forces and Rigid-Body Velocities using Observers"; IEEE International Conference on Roboticxs and Automation San Dier, CA 1994.

R. V. Dubey, T.F. Chan, S.E. Everett; Variable Damping Impedance control of a Bilateral Telerobotic System *Control Systems Magazine, IEEE*; Publication Date: Feb. 1997 vol. 17, Issue: 1; pp. 37-45.

K. H. Zaad, S.E. Salcudean ;"Analisys and Evaluation of Stability and Performance Robustness for Teleoperation Control Architectures"; Proceeding of 2000IEEE International Conference on Robotics and Automarion, San Francisco CA. Apr. 2000.

Y. Yokokohji, T. Imaida, T. Yoshikawa ; "Bilateral Control with Energy Balance Monitoring Under Time-Varying Communication Delay" proceeding of 2000IEEE International Conference on Robotics&Automation San Francisock CA Apr. 2000.

F. Feffard, E. Andriot; A. Micaelli; On the Use of a Base Force/Torque Sensor In Teleoperation Proceeding of 2000 IEEE International Conference on Robotics & Automation; San Francisco, CA Apr. 2000.

Speich; Joehn E; Fite, Kevin; Goldfarb, Michael; "A Methof for Simultaneously Increasing Transparencey and Stability Robustness in Bilateral Telemanipulations"; Proceeding of 2000 IEEE International Conference on Robotics & Automation; San Francisco, CA Apr. 2000.

Teleoperation Based on the Adjoint Jacobian Approach Y. Tsumaki, D.N. Nenchev, S. Kotera, M. Uchiyama; : *Control Systems Magazine, IEEE*; Date: Feb. 1997vol. 17, Issue: 1; 53-62.

B. Hannaford A;"Design Framework for Teleoperators with Kinesthetic Feedback"; IEE Transactions on Robotics and Automation, vol. 5 No. 4;Sep. 1989.

Jaydeep Roy, Lous L. Whitcomb;"Adaptive Force Control of Position/Velocity Controlled Robots: Theory and Experiments" *Robotics and Automation, IEEE Transactions*; Apr. 2002vol. 18, Issue: 2 pp. 121-137.

Jaydeep Roy, D. Rothbaum, Louis Whitcomb Haptic Feedback Augmentation through Position Based Adaptive Force Scaling: Theory and Experiments 2002 IEEE/RSJ Intl Conference on Intelligent Robots and Systems EPFL Lausane, Switzerland; Oct. 2002.

G.M.Prisco, M.Bergamasco ;Preliminary Considerations on the Design of Controllers for Haptic Interfaces Proceedings of SPIE—vol. 3206 Telemanipulator and Telepresence Technologies IV, Matthew R. Stein, Editor, Dec. 1997, pp. 2-11.

J. K. Salisbury; "Active stiffness control of manipulator in cartesian coordinates" $19^{TH}$ IEEE Confererenco on Decision & Control ; 1980 95-100.

C. Natale R. Koeppe; "An Automatic Procedure for Force Controller Design"; dlr Oberpfaffenhofen, Institute Report IB 515-99-05, 1999.

R. Volpe, P. Khosla ; "The Equivalence of Second-Order Impedance Control and Proportional Gain Explicit Force Control" The international joural of robotics research,, vol. 14 No. 6 Dec. 1995, pp. 574-589.

Murat Cenk Cavusoglu, Alana Sherman, Frank Tendick ; "Design of Bilateral Teleoperation Controllers for Haptic Exploration and Telemanipulation of Soft Environments" *Robotics and Automation, IEEE Transactions* ;Aug. 2002;vol. 18, Issue: 4 641-647.

S.E. Salcudean, W. H. Zhu, P. Abolmaesumi, S. Bachmann and P.D. Lawrence ; "A Robot System for Medical Ultrasound" Department of Electrical and Computer Engineering . . . www.ece.ubc.ca/~tims/pubs/ISRR99Salcudean.pdf.

Alin Albu-Schaffer, Gerd Hirzinger ; "Cartesian Impedance Control Techniques for Torque Controlled Light-Weight Robots", 2002 IEEE International Conference on Robotics & Automation; Washington DC May 2002.

Hyosig Kang and John T. Wen,; "Robotic Assistants Aid Surgeons During Minimally Invasive Procedures" Hyosig Kang and John T. Wen, IEE Magazine of Engineering in Medicine and Biology, Jan./Feb. 2001.

Hirche, Sandra & Buss, Martin; "Passive Position Controlled Tlepresence Systems Fwith Time Delay"; American Control Conference, 2003. Proceedings of the 2003, 2003—ieeexplore.ieee.org.

Kuchenbecker, Katherine J & Niemeyer, G; 2004 ASME Congress and RD&d Expo ; Anaheim, CA Nov. 11-19, 2004.

Abbott, J.J., and Okamura, A.M.; "Generating a State-Space Formulation of a Class of Telemanipulator," Haptic Exploration Lab Technical Report 03-1, The Johns Hopkins University, Jun. 1, 2003, <http://www.haptics.me.jhu.edu/publications/tech03-1-abbott.pdf>.

Abbott, J.J., and Okamura, A.M.; Analysis of virtual fixture contact stability for telemanipulation, Proceedings. 2003 IEEE/RSJ International Conference on Intelligent Robots and Systems, IROS 2003, vol. 3, Oct. 27-31, 2003, pp. 2699-2703.

Albu-Schaffer, A., and Hirzinger, G., "Cartesian Impedance Control Techniques for Torque Controlled Light-Weight Robots." Proceedings. IEEE International Conference on Robotics and Automation, ICRA '02, vol. 1, May 11-15, 2002 pp. 657-663 vol. 1.

Anderson and Spong, "Bilateral Control of Teleoperators with Time Delay," IEEE Transactions on Automatic Control, vol. 34, No. 5, May 1989, pp. 494-501.

Arcara, P., et al., "Intrinsically Passive Control in Bilateral Teleoperation Mimi Systems," Proceedings of the European Control Conference 2001 (ECC2001), p. 1180-1185, Porto, Portugal.

Cavusoglu, M.C., "Control of a Telesurgical Workstation," Master of Science, Plan II in Department of Electrical Engineering and Computer Sciences, Univ. of California at Berkeley, 1997, 66 pages.

Cavusoglu, M.C., et al., "A laparoscopic Telesurgical Workstation," IEEE Transactions on Robotics and Automation, vol. 15, No. 4, Aug. 1999, pp. 728-739.

Cavusoglu, M.C., et al., "Bilateral Controller Design for Telemanipulation in Soft Environments," Proceedings of the IEEE International Conference on Robotics and Automation (ICRA 2001), Seoul, Korea, May 21-26, 2001, 8 pages.

Cavusoglu, M.C., et al., "Design of Bilateral Teleoperation Controllers for Haptic Exploration and Telemanipulation of Soft Environments," IEEE Transactions on Robotics and Automation, vol. 18, Issue 4, Aug. 2002 pp. 641-647.

Dubey, R.V., et al., "Variable Damping Impedance control of a Bilateral Telerobotic System," IEEE Control Systems Magazine, vol. 17, Issue 1, Feb. 1997 pp. 37-45.

Flemmer, H., et al., "Passivity Issues in Bilateral Teleoperation—a Phase Property," EuroHaptics 2003, Dublin, Ireland, Jul. 6-9, 2003, 14 pages, Internet <http://www.eurohaptics.vision.ee.ethz.ch/2003.shtml>.

Funda, J., et al., "Constrained Cartesian Motion Control for Teleoperated Surgical Robots," IEEE Transactions on Robotics and Automation, (Jun. 1996) vol. 12, No. 3, pp. 453-465.

Geffard. F., et al., "On the Use of a Base Force/Torque Sensor In Teleoperation," Proceedings. IEEE International Conference on Robotics and Automation, 2000. ICRA '00. vol. 3, Apr. 24-28, 2000 pp. 2677-2683, vol. 3.

Hacksel, P.J. and S.E. Salcudean, "Estimation of Environment Forces and Rigid-Body Velocities using Observers," Proceedings, 1994 IEEE International Conference on Robotics and Automation, May 8-13, 1994 pp. 931-936, vol. 2.

Hannaford, B., "A Design Framework for Teleoperators with Kinesthetic Feedback," IEEE Transactions on Robotics and Automation, vol. 5, Issue 4, Aug. 1989 pp. 426-434.

Hashtrudi-Zaad, K.H., et al., "Bilateral Parallel Force/Position Teleoperation Control," 1999 Symp. Haptic Interfaces for Virtual Environments and Teleoperation Systems, Intl. Mech. Eng. Congr. Exp., (ASME Winter Annual Meeting), Nashville, TN, Nov. 1999, DSC Vol., pp. 351-358.

Hashtrudi-Zaad, K.H. and Salcudean, S.E., "Analysis and Evaluation of Stability and Performance Robustness for Teleoperation Control Architectures," IEEE International Conference on Robotics and Automation, 2000. Proceedings. ICRA '00. vol. 4, Apr. 24-28, 2000 pp. 3107-3113 vol. 4.

Hashtrudi-Zaad, K.H., and S.E. Salcudean, "Transparency in Time-Delayed Systems and the Effect of Local Force Feedback for Transparent Teleoperation," IEEE Transactions on Robotics and Automation, vol. 18, No. 1, Feb. 2002, pp. 108-114.

Hirche, S., and Buss, M., "Passive position controlled telepresence systems with time delay," Proceedings of the 2003 American Control Conference, 2003. vol. 1, Jun. 4-6, 2003 pp. 168-173 vol. 1.

Itoh, T., et al., "Human-Machine Cooperative Telemanipulation with Motion and Force Scaling Using Task-Oriented Virtual Tool Dynamics," IEEE Transactions on Robotics and Automation, vol. 16, Issue 5, Oct. 2000 pp. 505-516.

Joly, L.D., et al., "Mechanical analogies in hybrid position/force control," Proceedings. 1997 IEEE International Conference on Robotics and Automation, Apr. 20-25, 1997 pp. 835-840 vol. 1.

Kang, H., and J.T. Wen, "Robotic Assistants Aid Surgeons During Minimally Invasive Procedures," IEEE Engineering in Medicine and Biology Magazine, vol. 20, Issue 1, Jan.-Feb. 2001 pp. 94-104.

Kuchenbecker, K.J., and G. Niemeyer, "Canceling Induced Master Motion in Force-Reflecting Teleoperation," Draft for IMECE Symposium on Advances in Robot Dynamics and Control; Published in Proceedings, vol. 2, Paper No. 60049, Nov. 2004.

Lawrence, D.A., "Stability and Transparency in Bilateral Teleoperation," IEEE Transactions on Robotics and Automation, vol. 9, Issue 5, Oct. 1993 pp. 624-637.

Mitsuishi, M., et al., "Tele-micro-surgery system with intelligent user interface," Proceedings. IEEE International Conference on Robotics and Automation, 2000. . ICRA '00, vol. 2, Apr. 24-28, 2000 pp. 1607-1614 vol. 2.

Natale, C., and R. Koeppe, "An Automatic Procedure for Force Controller Design" Proceedings.1999 IEEE/ASME International Conference on Advanced Intelligent Mechatronics, Sep. 19-23, 1999 pp. 967-972.

Prisco, G.M., et al., "Preliminary Considerations on the Design of Controllers for Haptic Interfaces," SPIE Proceedings, Telemanipulator and Telepresence Technologies IV, Ed. Stein, Matthew R., Oct. 14-17, 1997, vol. 3206, pp. 2-11.

Repperger, "Active Force Reflection Devices in Teleoperation," IEEE Control Systems Magazine, vol. 11, Issue 1, Jan. 1991 pp. 52-56.

Rosen, J., et al., "Force Controlled and Teleoperated Endoscopic Grasper for Minimally Invasive Surgery- Experimental Performance Evaluation," IEEE Transactions on Biomedical Engineering, vol. 46, Issue 10, Oct. 1999 pp. 1212-1221.

Roy, J. and Whitcomb, L.L., "Adaptive Force Control of Position/Velocity Controlled Robots: Theory and Experiment," Submitted for Review, IEEE Transactions on Robotics and Automation, published in vol. 18, Issue 2, Apr. 2002 pp. 121-137.

Roy, J., et al., "Haptic Feedback Augmentation through Position Based Adaptive Force Scaling: Theory and Experiments," IEEE/RSJ International Conference on Intelligent Robots and System, 2002. vol. 3, Sep. 30-Oct. 5, 2002 pp. 2911-2919 vol. 3.

Ryu, J.H., et al., "Stable Teleoperation with Time Domain Passivity Control," Internet <brl.ee.washington.edu/publications/Rep154.pdf> 6 pages, 2002.

Salcudean, et al., "Performance Measurement in Scaled Teleoperation for Microsurgery," Proc. of First Joint Conf., Computer Vision, Virtual Reality and Robotics in Medicine and Medical Robotics and Computer-Assisted Surgery, CVRMed-MRCAS'97, Grenoble, France, Mar. 19-22, 1997; J. Troccaz, E. Grimson, R. Mosges (Eds.), pp. 789-798, Springer-Verlag Lecture Notes in Computer Science, vol. 1205.

Salcudean, S.E., et al., "A Robot System for Medical Ultrasound," Robotics Research, the 9th International Symposium of Robotics Research (ISRR'99), J.M. Hollerbach and D.E. Koditschek (Eds.), pp. 195-202, Springer 2000.

Salcudean, S.E., et al., "Transparent Bilateral Teleoperation under Position and Rate Control", Intl. J. Robotics Research, vol. 19, No. 12, Dec. 2000, pp. 1185-1202.

Salisbury, K., "Active stiffness control of manipulator in Cartesian coordinates," In 19th IEEE Conference on Decision and Control, 1980. pp. 95-100.

Sherman, et al., "Comparison of Teleoperator Control Architectures for Palpation Task," Proceedings of IMECE'00, Symp. on Haptic Interfaces for Virtual Environment and Teleoperator Systems, Nov. 5-10, 2000, Orlando, FL, 8 pages.

Speich, J.E., et al., "A Method for Simultaneously Increasing Transparency and Stability Robustness in Bilateral Teleoperation," Proceedings. IEEE International Conference on Robotics and Automation, 2000. ICRA '00. vol. 3, Apr. 24-28, 2000, pp. 2671-2676 vol. 3.

Stramigioli, S., "Geometric Scattering in Tele-manipulation of Port Controlled Hamiltonian Systems," Submitted to 39th IEEE Conference on Decision and Control, Dec. 12-15, 2000. Sydney, Australia.

Tendick, et al., "Maximizing the Sensation of Compliance in Teleoperative Surgery," Submitted to the Eighth International Symposium on Robotics with Applications, part of the World Automation Congress (WAC 2000), Maui, HI, Jun. 11-16, 2000, 10 pages.

Tsumaki, Y., et al., "Teleoperation Based on the Adjoint Jacobian Approach," IEEE Control Systems Magazine, vol. 17, Issue 1, Feb. 1997 pp. 53-62.

Volpe, R. and P.K. Khosla, "The Equivalence of Second-Order Impedance Control and Proportional Gain Explicit Force Control," International Journal of Robotic Research (IJRR), vol. 14, No. 6, pp. 574-589, Dec. 1995.

Yokokohji and Yoshikawa, "Bilateral Control of Master-Slave Manipulators for Ideal Kinesthetic Coupling- Formulation and Experiments," IEEE Transactions on Robotics and Automation, vol. 10, No. 5, Oct. 1994, pp. 605-620.

Yokokohji, Y. et al., "Bilateral Control with Energy Balance Monitoring Under Time-Varying Communication Delay," Proceedings. IEEE International Conference on Robotics and Automation, 2000. ICRA '00. vol. 3, Apr. 24-28, 2000 pp. 2684-2689 vol. 3.

Zhu, W.H. and S.E. Salcudean, "Teleoperation with Adaptive Motion/Force Control," IEEE International Conference on Robotics and Automation (ICRA), pp. 231-237, Detroit, MI, May 1999.

Zhu, W.H., and S.E. Salcudean, "Stability Guaranteed Teleoperation: an Adaptive Motion/Force Control Approach," IEEE Transactions on Automatic Control, vol. 45, Issue 11, Nov. 2000 pp. 1951-1969.

Zhu, W.H., et al., "Experiments with Transparent Teleoperation under Position and Rate Control," Proceedings of IEEE International Conference on Robotics and Automation (ICRA), 1999, vol. 3, May 10-15, 1999 pp. 1870-1875.

* cited by examiner

US 7,689,320 B2

ROBOTIC SURGICAL SYSTEM WITH JOINT MOTION CONTROLLER ADAPTED TO REDUCE INSTRUMENT TIP VIBRATIONS

CROSS REFERENCE TO RELATED APPLICATIONS

This application claims priority to U.S. provisional application Ser. No. 60/751,947 filed Dec. 20, 2005, which is incorporated herein by reference.

FIELD OF THE INVENTION

The present invention generally relates to robotic surgical systems and in particular, to a robotic surgical system with joint motion controller adapted to reduce surgical instrument tip vibrations without significantly degrading control system stability.

BACKGROUND OF THE INVENTION

Robotic surgical systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using robotic surgical systems is strong and growing.

One example of a robotic surgical system is the da Vinci® Surgical System from Intuitive Surgical, Inc., of Sunnyvale, Calif. The da Vinci® system includes a surgeon's console, a patient-side cart, a high performance 3-D vision system, and Intuitive Surgical's proprietary EndoWrist™ articulating instruments, which are modeled after the human wrist so that when added to the motions of the robotic arm assembly holding the surgical instrument, they allow a full six degrees of freedom of motion, which is comparable to the natural motions of open surgery.

The da Vinci® surgeon's console has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The surgeon sits comfortably and looks into this display throughout surgery, making it an ideal place for the surgeon to display and manipulate 3-D intraoperative imagery.

While performing a surgical procedure, vibrations experienced on a tip of a surgical instrument may cause control problems for a surgeon. For example, such vibrations may make it difficult for the surgeon to perform fine surgical manipulations of tissue, needles and sutures. A flexible robotic arm assembly, especially when mounted on flexible setup arms and/or with unbalanced link masses and inertias, may cause such vibrations to easily get started by fast transient motions commanded by the surgeon on a master manipulator. The vibrations in this case may be at the resonant frequency of the robotic arm assembly, or that of a mechanical structure supporting the robotic arm assembly. In addition, vibrations may also occur as a result of any non-smooth command motion of the master manipulator.

Although a low pass filter may be employed in a teleoperation control system to filter out master manipulator motion commands that may cause vibration occurring at frequencies above those of intended surgical motion, such a low pass filter also inserts delay into the teleoperation system, specifically between the master commanded motion and the actual robotic arm assembly motion. Unfortunately, when force feedback indicative of forces being asserted against the tip of the surgical instrument is provided back to the surgeon through the master manipulator, the delay added to the teleoperation control system by the low pass filter tends to drive the control system unstable. This greatly limits either the ability to filter out undesirable vibrations or the ability of the system to provide the surgeon with haptic force feedback.

OBJECTS AND SUMMARY OF THE INVENTION

Accordingly, an object of aspects of the present invention is a robotic arm assembly joint controller for reducing vibrations that may otherwise be experienced on a tip of a surgical instrument during a surgical procedure without adding undue delay.

Another object of aspects of the present invention is a robotic arm assembly joint controller for reducing vibrations that may otherwise be experienced on a tip of a surgical instrument during a surgical procedure, and providing force feedback indicative of forces being asserted against the instrument tip back to a surgeon performing the procedure without jeopardizing control system stability.

These and additional objects are accomplished by the various aspects of the present invention, wherein briefly stated, one aspect is a robotic surgical system comprising: a surgical instrument; a robotic arm assembly holding the surgical instrument; a master manipulator; and a controller configured to control movement of the surgical instrument in response to user operation of the master manipulator in such a manner that vibrations experienced at a tip of the surgical instrument are reduced by filtering an output of the master manipulator that may induce the vibrations while at least partially compensating in a feedback path back to the master manipulator for delay induced by such filtering so as to enhance stability of such control.

Another aspect is a control system included in a controller for controlling movement of a robotic arm assembly in response to user manipulation of a master manipulator, wherein the control system controls rotation of a slave joint of the robotic arm assembly. The control system comprises: a filter in a forward control path defined as being from the master manipulator to a motor coupled to the slave joint, wherein the filter attenuates frequency content of a joint position command generated from user manipulation of the master manipulator so that vibrations experienced at a tip of a surgical instrument held by the robotic arm assembly are reduced; and an inverse filter in a feedback path defined as being from a slave joint sensor to the master manipulator, wherein the slave joint sensor senses movement of the slave joint and the inverse filter provides a phase lead in the feedback path so as to at least partially compensate for a phase lag caused by the filter.

Another aspect is a method for controlling the movement of a slave joint in a robotic arm assembly, comprising: generating filtered position, velocity and acceleration slave joint commands so as to command movement of the slave joint while reducing vibrations experienced on a tip of a surgical instrument held by the robotic arm assembly; generating a motor command signal using the filtered position, velocity and acceleration slave joint commands; providing the motor command signal to a motor coupled to the slave joint; receiving sensed positions of the slave joint; generating estimated positions, velocities and accelerations of the slave joint using the sensed positions of the joint and the motor command signal; and updating the motor command signal using a function of the differences between the filtered position, velocity and acceleration slave joint commands and the estimated positions, velocities and accelerations of the slave joint.

Still another aspect is a method for reducing vibrations on a tip of a surgical instrument held by a robotic arm assembly without degrading stability of a control system controllably moving a slave joint of the robotic arm assembly. The method comprises: attenuating a first signal indicating slave joint position commands generated from user manipulation of a master manipulator at frequencies beyond a cut-off frequency so that vibrations on the tip of the surgical instrument held by the robotic arm assembly are reduced at those frequencies; and amplifying a second signal indicating a position of the slave joint at frequencies above the cut-off frequency while providing phase lead to the second signal so as to at least partially compensate for delay caused by the attenuation of the first signal and stably generate a feedback signal provided to the master manipulation.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
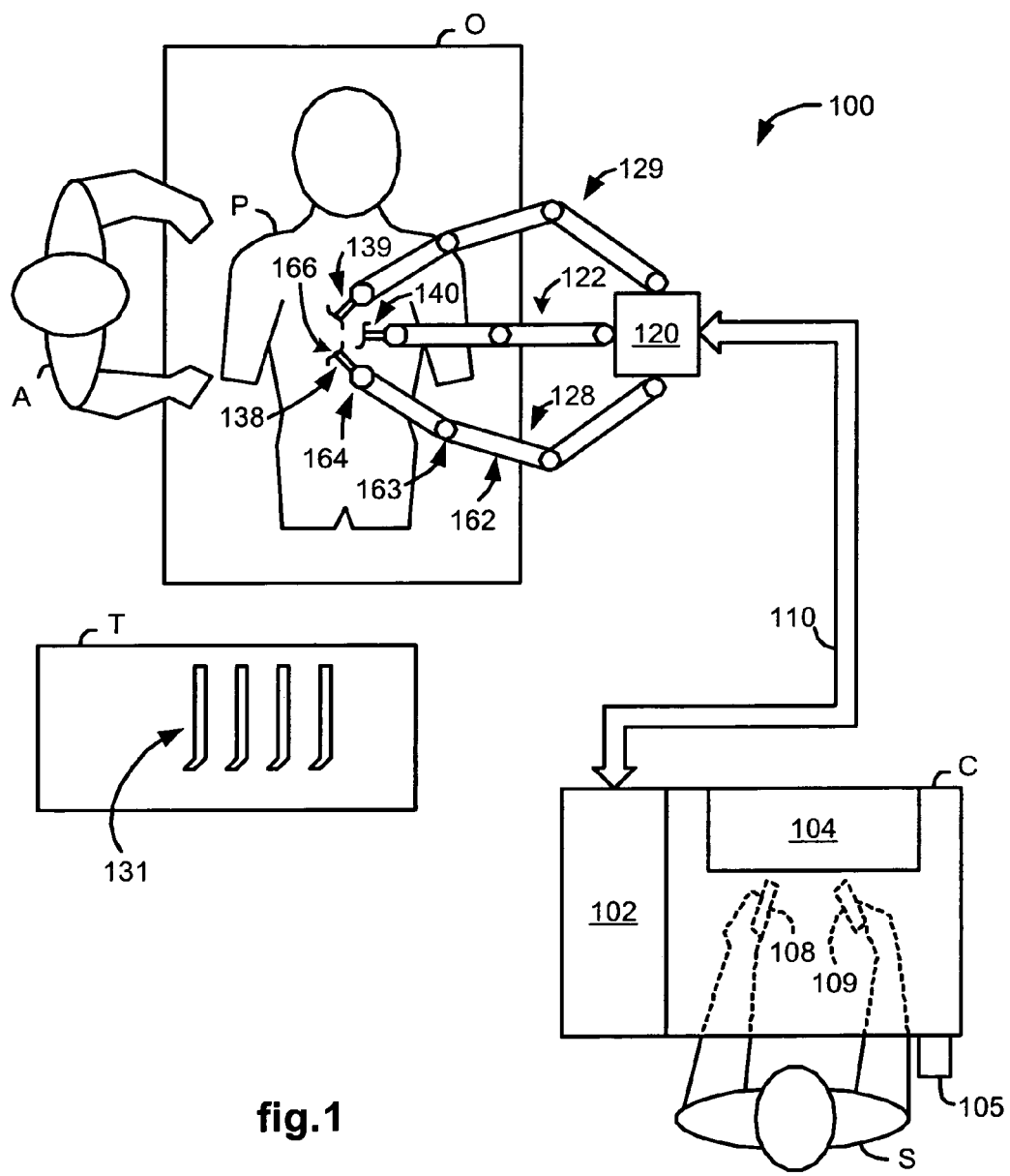
FIG. 1 illustrates a top view of an operating room employing a robotic surgical system utilizing aspects of the present invention.

FIG. 1 illustrates, as an example, a top view of an operating room employing a robotic surgical system. The robotic surgical system in this case is a robotic surgical system 100 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 104 for displaying an image of a surgical site to the Surgeon, left and right manipulatable control devices 108 and 109, a foot pedal 105, and a processor 102. The control devices 108 and 109 may include any one or more of a variety of input devices such as joysticks, gloves, trigger-guns, hand-operated controllers, or the like. The processor 102 is preferably a dedicated computer that may be integrated into the Console or positioned next to it.

The Surgeon performs a minimally invasive surgical procedure by manipulating the control devices 108 and 109 (also referred to herein as "master manipulators") so that the processor 102 causes their respectively associated robotic arm assemblies, 128 and 129, (also referred to herein as "slave manipulators") to manipulate their respective removably coupled surgical instruments 138 and 139 (also referred to herein as "tools") accordingly, while the Surgeon views the surgical site in 3-D on the Console monitor 104 as it is captured by a stereoscopic endoscope 140.

Each of the tools 138 and 139, as well as the endoscope 140, is preferably inserted through a cannula or other tool guide (not shown) into the Patient so as to extend down to the surgical site through a corresponding minimally invasive incision such as incision 166. Each of the robotic arms is conventionally formed of links, such as link 162, which are coupled together and manipulated through motor controlled or active joints, such as joint 163.

The number of surgical tools used at one time and consequently, the number of robotic arms being used in the system 100 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 131 from a Tray ("T") in the operating room.

Preferably, the monitor 104 is positioned near the Surgeon's hands so that it will display a projected image that is oriented so that the Surgeon feels that he or she is actually looking directly down onto the operating site. To that end, images of the tools 138 and 139 preferably appear to be located substantially where the Surgeon's hands are located.

The processor 102 performs various functions in the system 100. One important function that it performs is to translate and transfer the mechanical motion of control devices 108 and 109 to their respective robotic arms 128 and 129 through control signals over bus 110 so that the Surgeon can effectively manipulate their respective tools 138 and 139. Another important function is to implement various control system processes as described herein.

Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware.

For additional details on robotic surgical systems, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are incorporated herein by these references.

Figure 2:
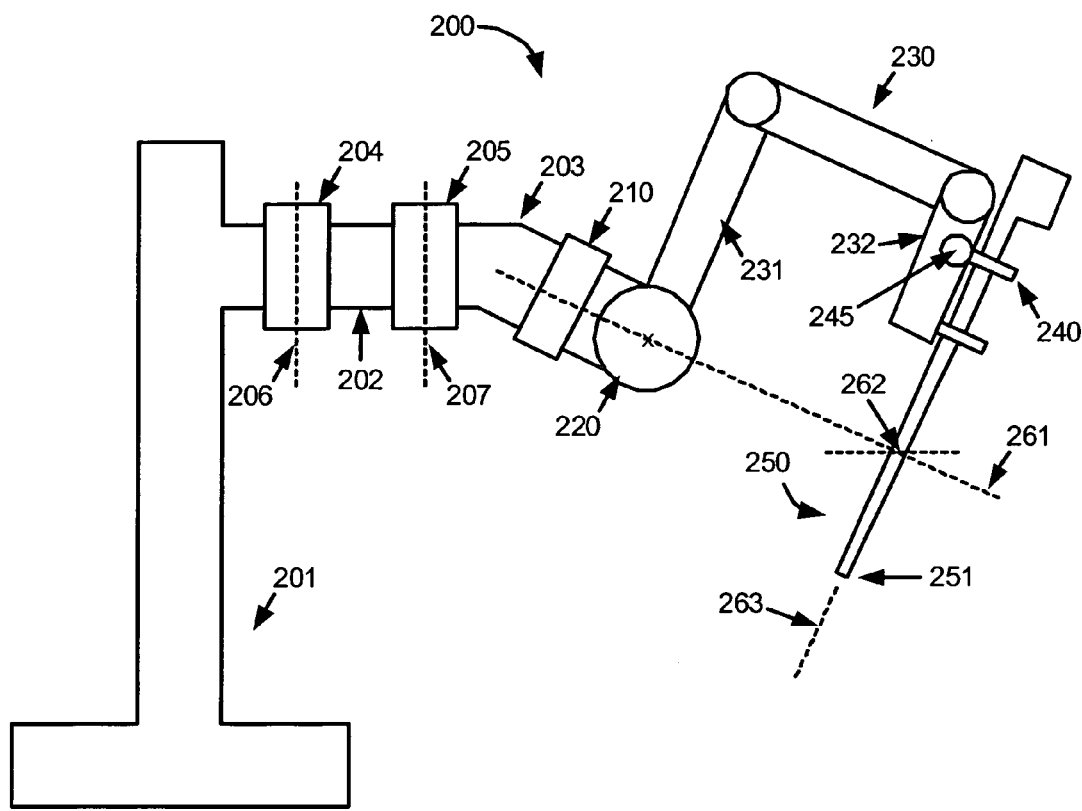
FIG. 2 illustrates a simplified side view of a robotic arm assembly that is usable with various aspects of the present invention.

FIG. 2 illustrates, as an example, a side view of a simplified (not necessarily in proportion or complete) robotic arm assembly 200 (which is representative of robotic arm assemblies 128 and 129) holding a surgical instrument 250 (which is representative of tools 138 and 139) for performing a surgical procedure. The surgical instrument 250 is removably held in tool holder 240. The arm assembly 200 is mechanically supported by a base 201, which may be part of a patient-side movable cart or affixed to the operating table or ceiling. It includes links 202 and 203 which are coupled together and to the base 201 through setup joints 204 and 205.

The setup joints 204 and 205 in this example are passive joints that allow manual positioning of the arm 200 when their brakes are released. For example, setup joint 204 allows link 202 to be manually rotated about axis 206, and setup joint 205 allows link 203 to be manually rotated about axis 207.

Although only two links and two setup joints are shown in this example, more or less of each may be used as appropriate in this and other robotic arm assemblies in conjunction with the present invention. For example, although setup joints 204 and 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The robotic arm assembly 200 also includes three active joints driven by motors. A yaw joint 210 allows arm section 230 to rotate around an axis 261, and a pitch joint 220 allows arm section 230 to rotate about an axis perpendicular to that of axis 261 and orthogonal to the plane of the drawing. The arm section 230 is configured so that sections 231 and 232 are always parallel to each other as the pitch joint 220 is rotated by its motor. As a consequence, the instrument 250 may be controllably moved by driving the yaw and pitch motors so as to pivot about the pivot point 262, which is generally located through manual positioning of the setup joints 204 and 205 so as to be at the point of incision into the patient. In addition, an insertion gear 245 may be coupled to a linear drive mechanism (not shown) to extend or retract the instrument 250 along its axis 263.

As noted, one problem with the robotic arm assembly 200 is the occurrence of vibrations on a tip 251 of the surgical instrument 250 that may cause control problems for a surgeon when performing a surgical procedure using the instrument 250. The vibrations may be triggered by dynamic reaction forces produced by the robotic arm assembly 200 during the motions of the surgical instrument 250. The vibrations may be amplified by resonance of the robotic arm assembly 200 or a mechanical structure supporting the robotic arm assembly 200, such as the base 201, at their respective resonant frequencies.

Although each of the yaw, pitch and insertion joints or gears, 210, 220 and 245, is controlled by an individual joint or gear controller, the three controllers are controlled by a common master/slave control system so that the robotic arm assembly 200 (also referred to herein as a "slave manipulator") may be controlled through user (e.g., surgeon) manipulation of its associated master manipulator.

Figure 3:
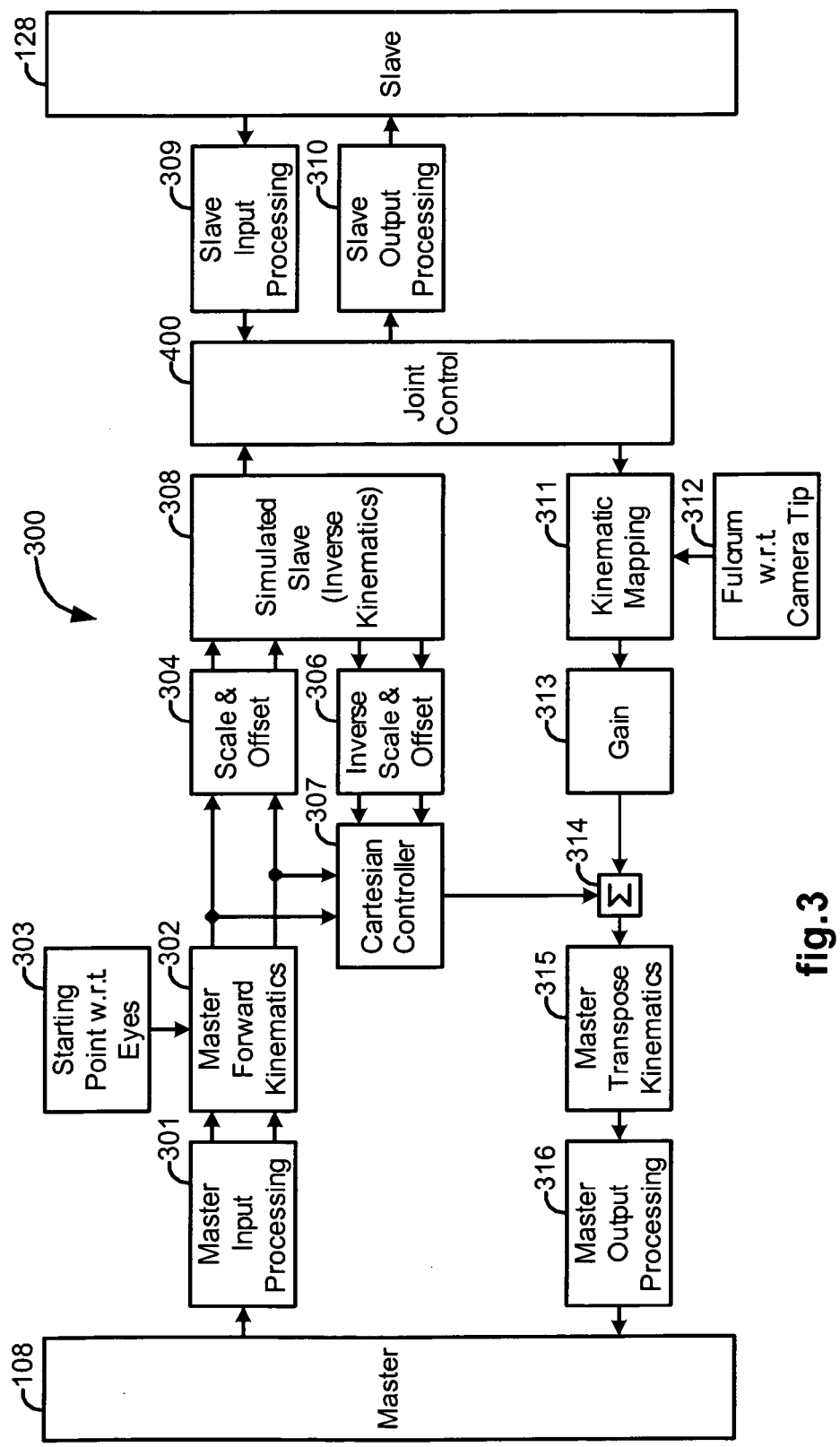
FIG. 3 illustrates a block diagram of a master/slave control system utilizing aspects of the present invention.

FIG. 3 illustrates, as an example, a block diagram of a master/slave control system 300 for controlling movement of the slave manipulator 128 and consequently, the position and orientation of its attached tool 138, as commanded by movement of the master manipulator 108 by a surgeon. A similar control system may also be provided for slave manipulator 129 and its associated master manipulator 109.

Both the master and slave manipulators, 108 and 128, include a number of linkages connected by joints so as to facilitate multiple degrees-of-freedom movement. As the surgeon moves the master manipulator 108 from one position to another during the course of performing a surgical procedure, sensors associated with the master manipulator joints provide information indicating such command movement in master joint space, and sensors associated with the slave manipulator joints provide information indicating slave manipulator 128 and consequently, tool 138 movement in slave joint space for feedback purposes.

A master input processing unit 301 receives the information of the master joint positions, which are sampled at the control system processing rate (e.g., 1300 Hz in the present example), from the master joint sensors in the master manipulator 108, and computes joint velocities from the sensed joint positions. A master forward kinematics processing unit 302 receives the master joint positions and velocities from the master input processing unit 301, transforms them from master joint space to corresponding positions and velocities of the master frame (i.e., the frame associated with the master manipulator 108) in Cartesian space relative to the eye reference frame (i.e., the reference frame associated with the position of the surgeon's eyes), using, for example, a Jacobian matrix and eye related information separately determined and provided in block 303.

A scale and offset processing unit 304 receives the Cartesian position and velocity commands from the master forward kinematics processing unit 302, scales the commanded movement according to a scale factor selected to perform the surgical procedure, and takes into account offsets to generate desired slave tool frame (i.e., the frame associated with the tool 138) positions and velocities. The scale adjustment is useful where small movements of the slave manipulator 128 are desired relative to larger movement of the master manipulator 108 in order to allow more precise movement of the slave tool 138 at the surgical site. The offsets, on the other hand, determine, for example, the corresponding position and/or orientation of an end effector frame (e.g., the frame associated with an end effector of the tool 138) in the camera reference frame (i.e., the frame associated with the distal tip of the endoscope 140) relative to a position and orientation of the master frame in the eye reference frame.

A simulated slave processing unit 308 receives desired slave tool frame position and velocity commands from the scale and offset processing unit 304, and limits the desired slave tool frame position, orientation and velocities, to assigned Cartesian Limits for instance to enforce correct and intuitive operation of the tool 138 by keeping it within its dexterous workspace. The simulated slave processing unit 308 generates simulated slave joint positions and velocities corresponding to the limited slave tool frame positions and velocities, while making sure that the generated slave joint positions and velocities do not exceed the actual slave joint's range of motion and maximum velocities (i.e., joint limits) even in the vicinity of kinematic singularities for the slave kinematics.

An inverse scale and offset processing unit 306 receives the simulated joint position and velocity commands from the simulated slave processing unit 308, and performs an inverse function to that of the scale and offset processing unit 304 on them. A Cartesian controller 307 receives as first inputs, the inputs to the scale and offset processing unit 304 and as second inputs, the outputs of the inverse scale and offset processing unit 306. The Cartesian controller 307 then generates an error signal as a difference of the first and second inputs, and a Cartesian force "$F_{CART}$" from the error signal such as with the following formula:

$$F_{CART}=K(\Delta x)+B(\Delta \dot{x}) \quad (1)$$

where "K" is a spring constant, "B" is a damping constant, "$\Delta \dot{x}$" is the difference between the Cartesian velocity inputs to the Cartesian controller 307 and "$\Delta x$" is the difference between the Cartesian position inputs to the Cartesian controller 307. For an orientation error, a corresponding torque in Cartesian space is determined.

A master transpose kinematics processing unit 315 receives the Cartesian force $F_{CART}$ through a summation node 314, and generates a corresponding torque in joint space using, for example, the Jacobian transpose matrix and kinematic relationships associated with the master manipulator 108. A master output processing unit 316 receives the master torque signals from the master transpose kinematics processing unit 315, generates electrical currents corresponding to the master torque signals, and supplies the electrical currents to corresponding master joint motors of the master manipulator 108. As a result, a surgeon operating the master manipulator 108 feels the Cartesian force, $F_{CART}$, whenever the surgeon is commanding a position or velocity which exceeds system Cartesian or slave joint limits, or would result in a kinematic singularity condition for the slave manipulator 128.

As the master input processing unit 301 is receiving master joint positions from sensors in the master manipulator 108, a slave input processing unit 309 is also receiving slave joint positions from position sensors in the slave manipulator 128 at the control system processing rate. A joint control unit 400 receives the slave joint positions from the slave input processing unit 309 and the simulated joint position commands provided from the simulated slave processing unit 308, and generates slave torque command signals for the slave joint motors and master torque feedback command signals for the master joint motors.

The slave torque command signals are generated by the joint control unit 400 so as to drive joints of the slave manipulator 128 until feedback errors calculated in the joint control unit 400 zero out, as will be described in further detail in reference to FIG. 4. A slave output processing unit 310 receives the slave torque command signals from the joint control unit 400, converts them into appropriate electrical currents, and supplies the electrical currents to the joint motors of the slave manipulator 128 so as to drive the motors accordingly.

The master torque feedback command signals are generated by the joint control unit 400 as a function of the slave joint position and velocity tracking errors so as to reflect forces being exerted against the tool 138 or its slave manipulator 128 back to the master manipulator 108 so that they may be felt by the surgeon. A kinematic mapping unit 311 receives the master torque feedback command signals from the joint control unit 400, and generates the corresponding Cartesian force at the tip of the tool 138 relative to the camera frame of the endoscope 140 using the slave kinematic configuration and the previously calculated slave fulcrum (e.g., pivot point) position information provided in block 312.

A gain 313 adjusts the magnitude of the Cartesian force so as to ensure system stability while providing adequate force sensation to the surgeon. The gain adjusted Cartesian force is then passed through the summation node 314, and processed along with the Cartesian force provided by the Cartesian controller 307 through the Master transpose kinematics processing unit 315 and Master output processing 316 as previously described in reference to their processing of the Cartesian force provided by the Cartesian controller 307.

Additional details related to conventional aspects of the master/slave control system 300, such as the various reference frames referred to herein and the calculation of the surgeon eye related information provided in block 303 and the slave fulcrum information provided in block 312, which are based upon well-known mathematics, are described, for example, in commonly owned U.S. Pat. No. 6,424,885, "Camera Referenced Control in a Minimally Invasive Surgical Apparatus," which is incorporated herein by this reference.

The joint control unit 400 includes a joint controller for each slave joint of the slave manipulator 128 that is being controlled by the master/slave control system 300. In particular, where the slave manipulator 128 includes a yaw joint 210, a pitch joint 220, and an insertion axis gear 245, such as the robotic arm assembly 200 of FIG. 2, each of these joints or gears will have its own controller.

Figure 4:
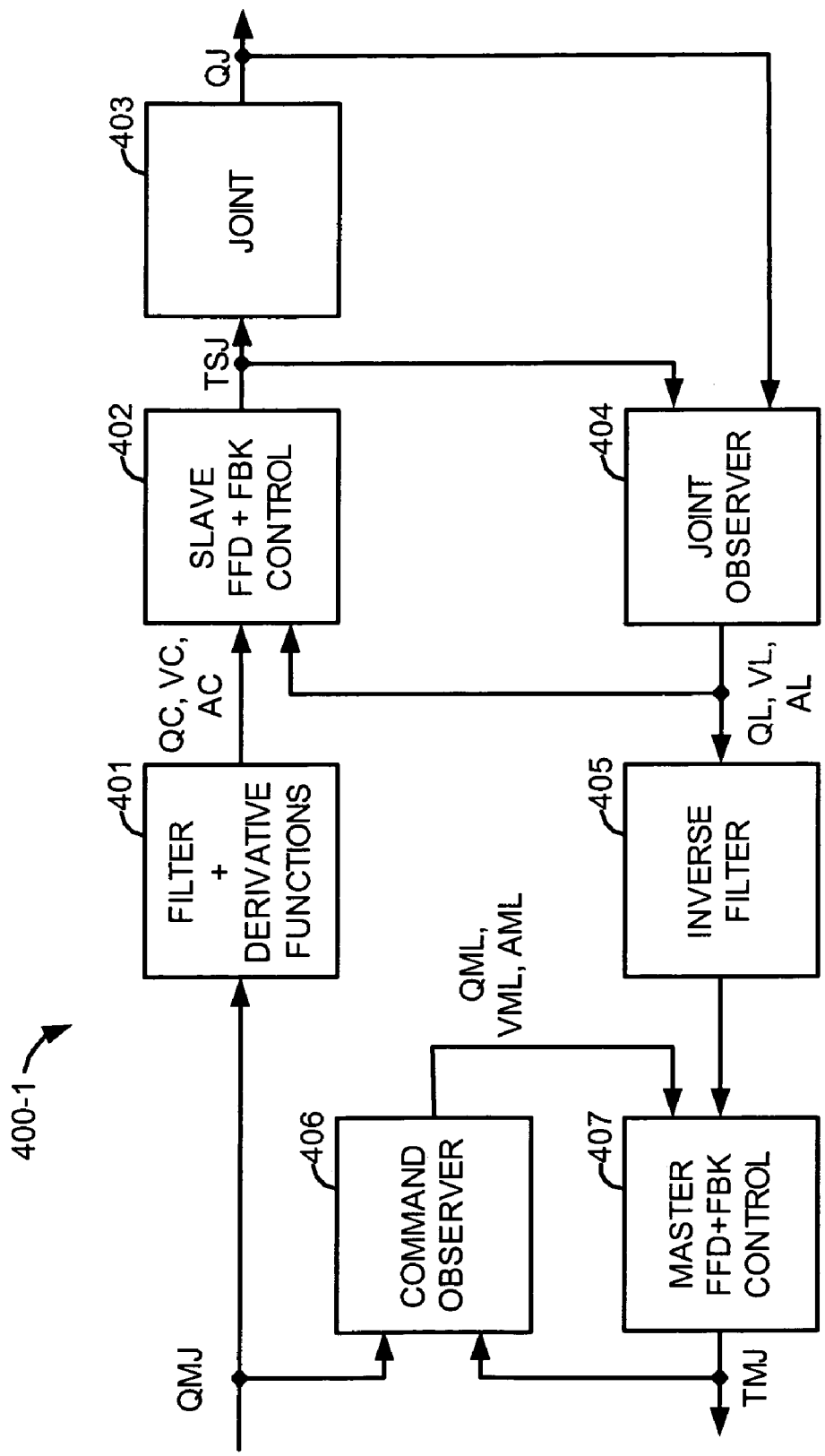
FIG. 4 illustrates a block diagram of a slave joint controller utilizing aspects of the present invention.

FIG. 4 illustrates, as an example, a block diagram of one such joint controller 400-1 (e.g., for controlling movement of either the yaw, pitch, or insertion joint or gear, 210, 220 or 245, of the robotic arm assembly 200), which has been adapted to reduce vibrations on the surgical instrument or end effector tip without overly degrading the stability of the control system 400 with force feedback. To simplify the description herein and in the claims, the term "joint" is to be understood to include gears as well as any other controllable component coupled to linear drive mechanisms that may be used in controlling robotic arm assemblies.

Figure 7:
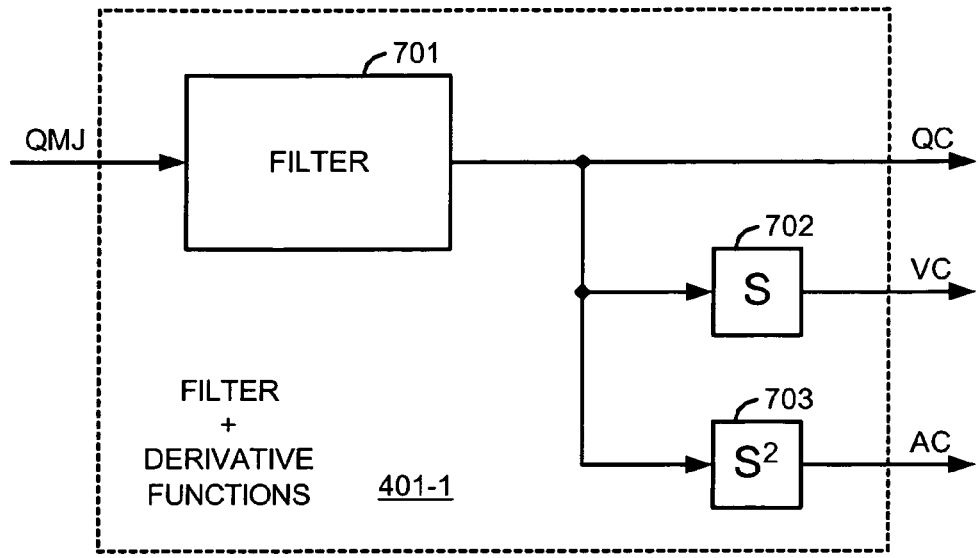
FIG. 7 illustrates a block diagram of a first filter/derivative function usable in a control system utilizing aspects of the present invention.
Figure 8:
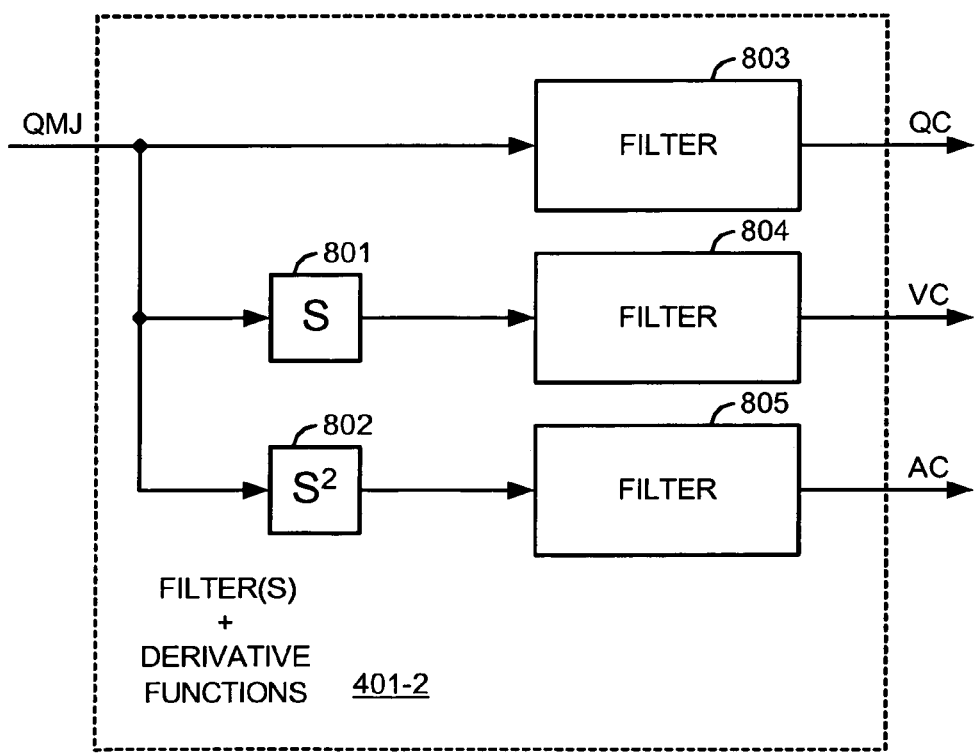
FIG. 8 illustrates a block diagram of a second filter/derivative function usable in a control system utilizing aspects of the present invention.

First, to reduce the vibrations at the tip of the instrument, an appropriate filter (plus derivative functions S and $S^2$) 401 is introduced into a forward path of the joint controller 400-1. The derivative functions are included, because the joint controller 400-1 employs a slave feedforward ("FFD") and feedback ("FBK") controller 402, which requires joint velocity and acceleration commands, as well as a joint position command. The controller 402 can be implemented as a proportional-integral-derivative ("PID") controller, a non-linear PID controller, or other controller including those having acceleration feedback and feedforward of the joint dynamics. The filter used in block 401 (e.g., 701 in FIG. 7 and 803, 804 and 805 in FIG. 8) is preferably a linear filter. The derivatives of a joint position command QMJ provided to the block 401 may be calculated after filtering of the joint position command QMJ as shown in FIG. 7, or they may be calculated before filtering of the joint position command QMJ as shown in FIG. 8. In the latter case, each of the joint position, velocity and acceleration commands may be individually filtered using the same or different filters, 803-805. Preferably, the block 401 (i.e., the filter+derivative functions) is a digital state space balanced realization using standard techniques for its conversion from the continuous domain to the digital domain (e.g., Tustin method, Euler method, etc.). The joint position command QMJ is one of the simulated joint position commands from the simulated slave processing unit 308. The filtered joint position, velocity and acceleration commands QC, VC and AC are then provided to the slave controller 402.

The filter (e.g., 701 in FIG. 7 or 803-805 in FIG. 8) is configured to attenuate frequencies beyond those reasonably expected to be commanded by user manipulation of the master manipulator 108. Since such intended surgical motion is generally found to be in the 0 to 3 Hz range, a 3 Hz cut-off frequency for the filter may be appropriate in a typical case.

To ensure a reasonably sharp cut-off, multiple poles at the cut-off frequency may be desired, such as two poles.

Since the filter in block 401 inserts delay into the joint controller 400-1, an inverse filter 405 is inserted in a feedback path to the master manipulator 108 to at least partially compensate for that delay. The inverse filter 405 is also preferably implemented in state space. In order to be the inverse of the forward path filter (e.g., 701 in FIG. 7 or 803-805 in FIG. 8), it is configured so as to have a reciprocal transfer function. Thus, it is characterized as amplifying its incoming signal starting at the same cut-off frequency as the forward path filter so as to add phase lead instead of lag.

To make the inverse filter 405 realizable, the forward path filter is designed so that it does not attenuate continuously after the cut-off frequency. Instead, it is preferably configured to attenuate at a constant level after reaching a predetermined attenuation level such as 12 dB.

Figure 9:
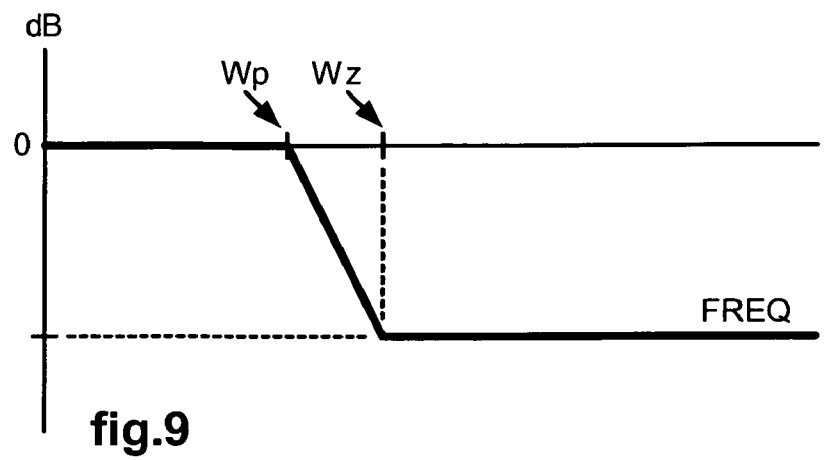
FIG. 9 illustrates a frequency diagram for a fixed attenuation filter usable in a control system utilizing aspects of the present invention.
Figure 11:
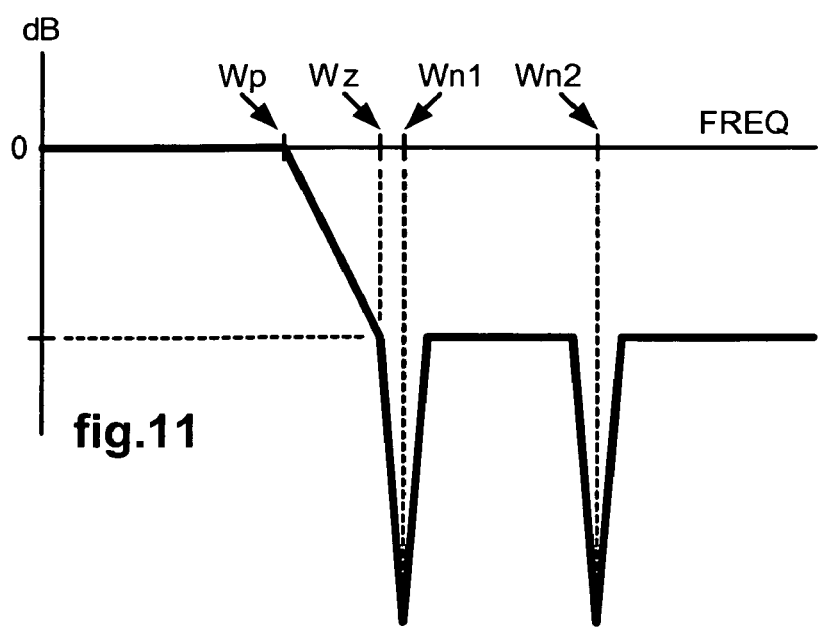
FIG. 11 illustrates a frequency diagram for a combination filter usable in a control system utilizing aspects of the present invention.
Figure 12:
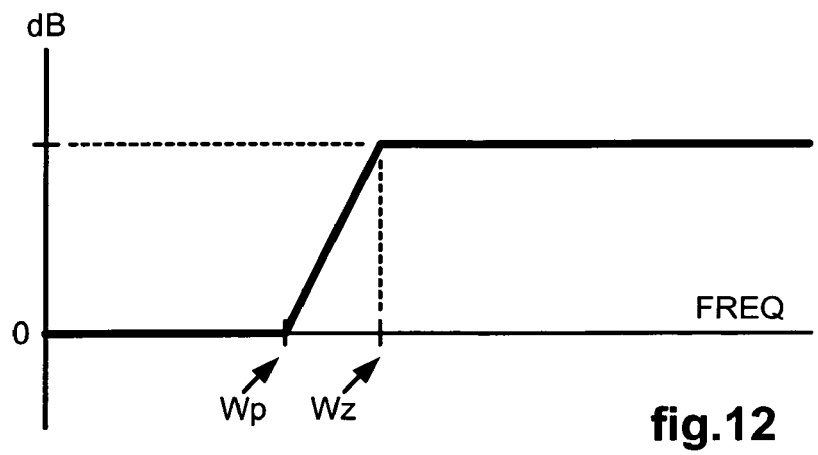
FIG. 12 illustrates a frequency diagram for an inverse fixed attenuation filter usable in a control system utilizing aspects of the present invention.
Figure 13:
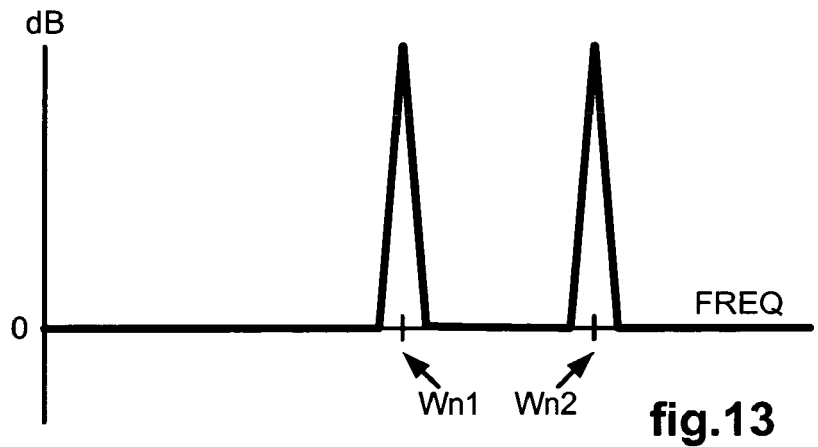
FIG. 13 illustrates a frequency diagram for an inverse dual frequency notch filter usable in a control system utilizing aspects of the present invention.

In a preferred embodiment of the inverse filter 405, the inverse filter is configured to have an equal number of poles and zeroes. Further, it has been found in certain applications that a forward path filter (e.g., 701 or 803-805) having two real poles and a pair of complex zeroes, provides good characteristics and a realizable and workable inverse filter 405. In this configuration, the complex zeroes define a frequency greater than the cut-off frequency defined by the real poles so that following that frequency, the attenuation remains constant. FIGS. 9 and 11 respectively illustrate examples for a forward path filter and inverse filter with the characteristics described thus far as having real poles at the frequency Wp and complex pair of zeroes at the frequency Wz, with all frequencies in radians.

Figure 10:
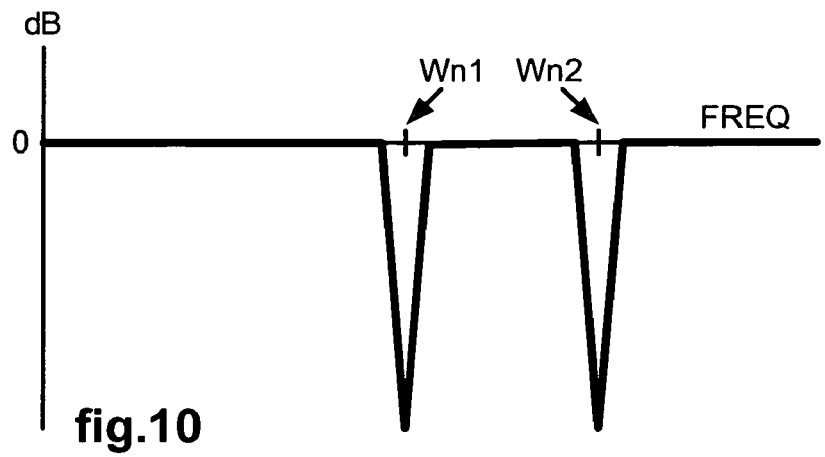
FIG. 10 illustrates a frequency diagram for a dual frequency notch filter usable in a control system utilizing aspects of the present invention.
Figure 14:
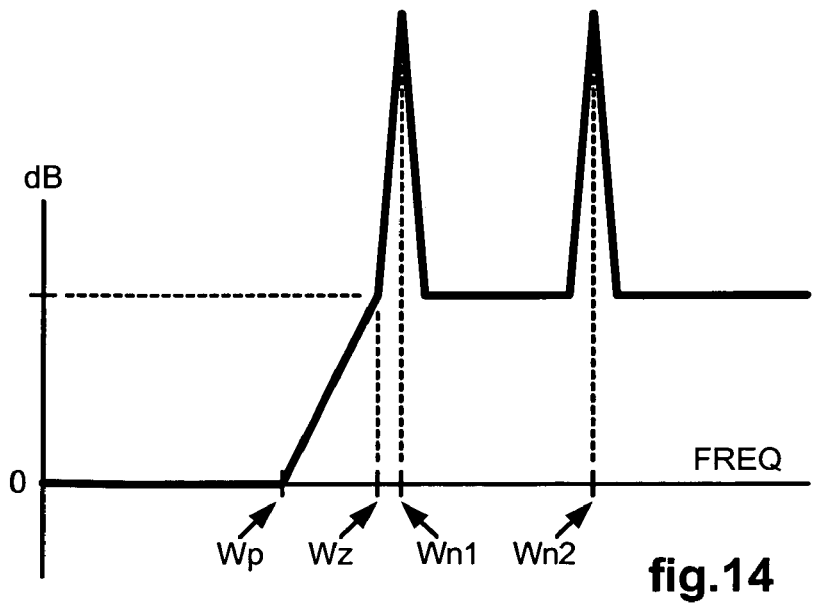
FIG. 14 illustrates a frequency diagram for an inverse combination filter usable in a control system utilizing aspects of the present invention.

In addition to having frequency characteristics such as shown in FIG. 9, the forward path filter also preferably includes notch filter characteristics such as shown in FIG. 10 to reduce the effects of resonant frequencies, Wn1 and Wn2, respectively of the robotic arm assembly and a mechanical structure supporting the robotic arm assembly. Consequently, when combining the filtering characteristics of FIGS. 9 and 10, the filtering characteristics as shown in FIG. 11 are those desired for the forward path filter, and in a similar fashion, the desired filtering characteristics of the inverse filter 405 are shown in FIG. 14.

The forward path filter may be represented in state space as the following:

$$X(k+1)=Ax(k)+Bu(k) \quad (2)$$

$$Y(k)=Cx(k)+Du(k) \quad (3)$$

wherein the input u=joint position command determined using inverse kinematics; the output y=filtered joint position, velocity and acceleration commands; the state x is preferably a vector having a length up to 7 by 1; and the matrices A, B, C and D are determined so as to provide the desired frequency characteristics, while having a balanced realization which improves numerical stability in floating point. The inverse filter 405 may be represented in state space form in a similar fashion.

Figure 5:
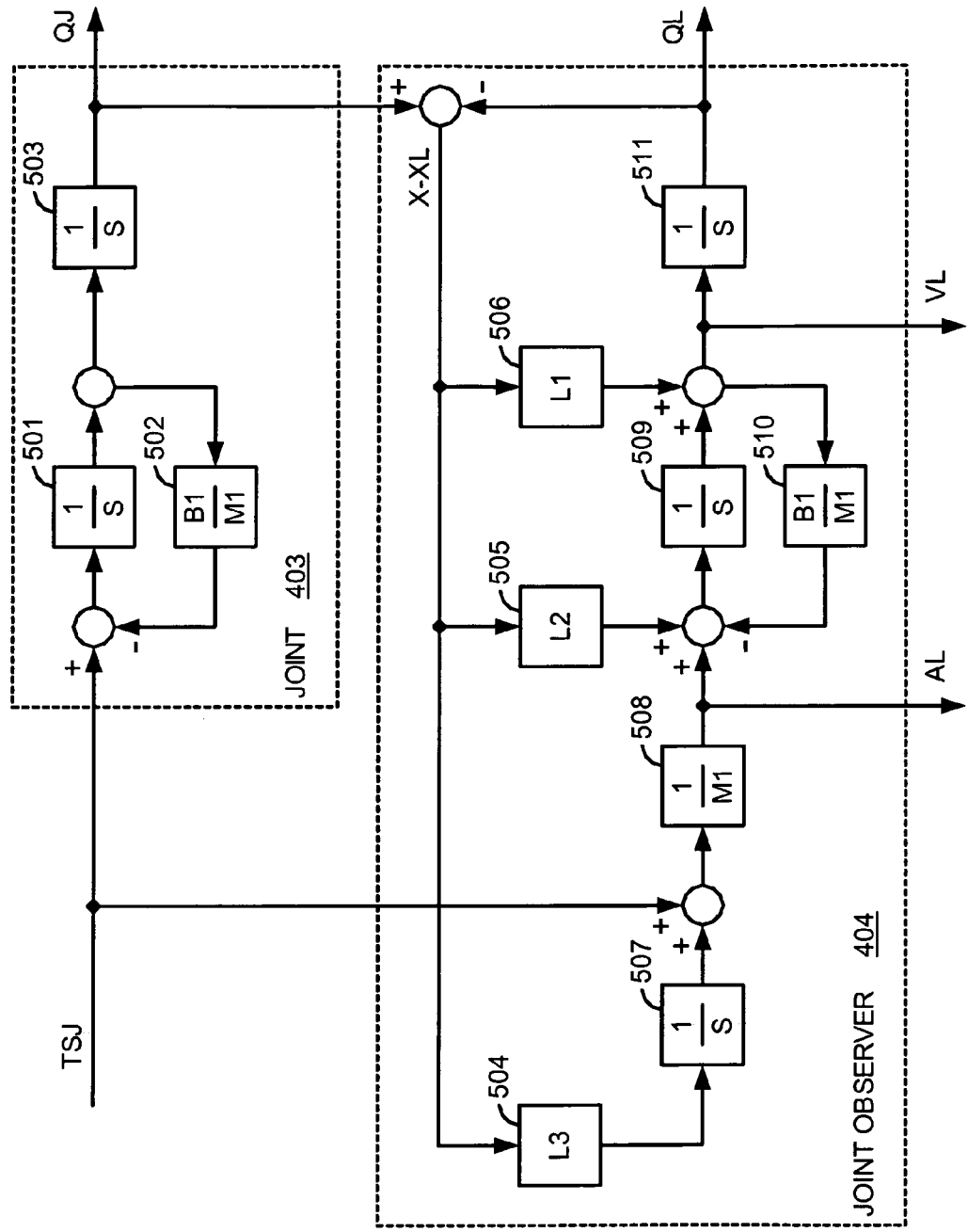
FIG. 5 illustrates a block diagram of a slave joint observer usable in a control system utilizing aspects of the present invention.

To further enhance the accuracy (by reducing noise) and stability (by reducing loop delays) of the joint controller 400-1 and/or master/slave control system 300, a joint observer 404 is preferably inserted so as to estimate actual joint positions, velocities and accelerations, QL, VL and AL, using sensed position indications QJ from an encoder or sensor coupled to the slave joint, and torque commands TSJ provided to drive the slave joint motor. The slave joint motor, slave joint, and slave joint sensor are all included and indicated in this example by reference number 403. An example of the joint observer 404 is shown configured as a disturbance observer structure in FIG. 5, wherein the parameters B1 and M1 come from a rigid model of the slave joint dynamics 403, and the parameters L1, L2 and L3 are selected empirically through simulation and/or system calibration to provide good observer dynamics and accuracy. Note that the outputs of the joint observer 404 are provided to the inverse filter 405 and the slave controller 402 so that differences between corresponding of the joint position QC, velocity VC and acceleration AC commands, and estimated joint position QL, velocity VL and acceleration AL may be computed by the slave controller 402 in generating the torque command signal TSJ.

Figure 6:
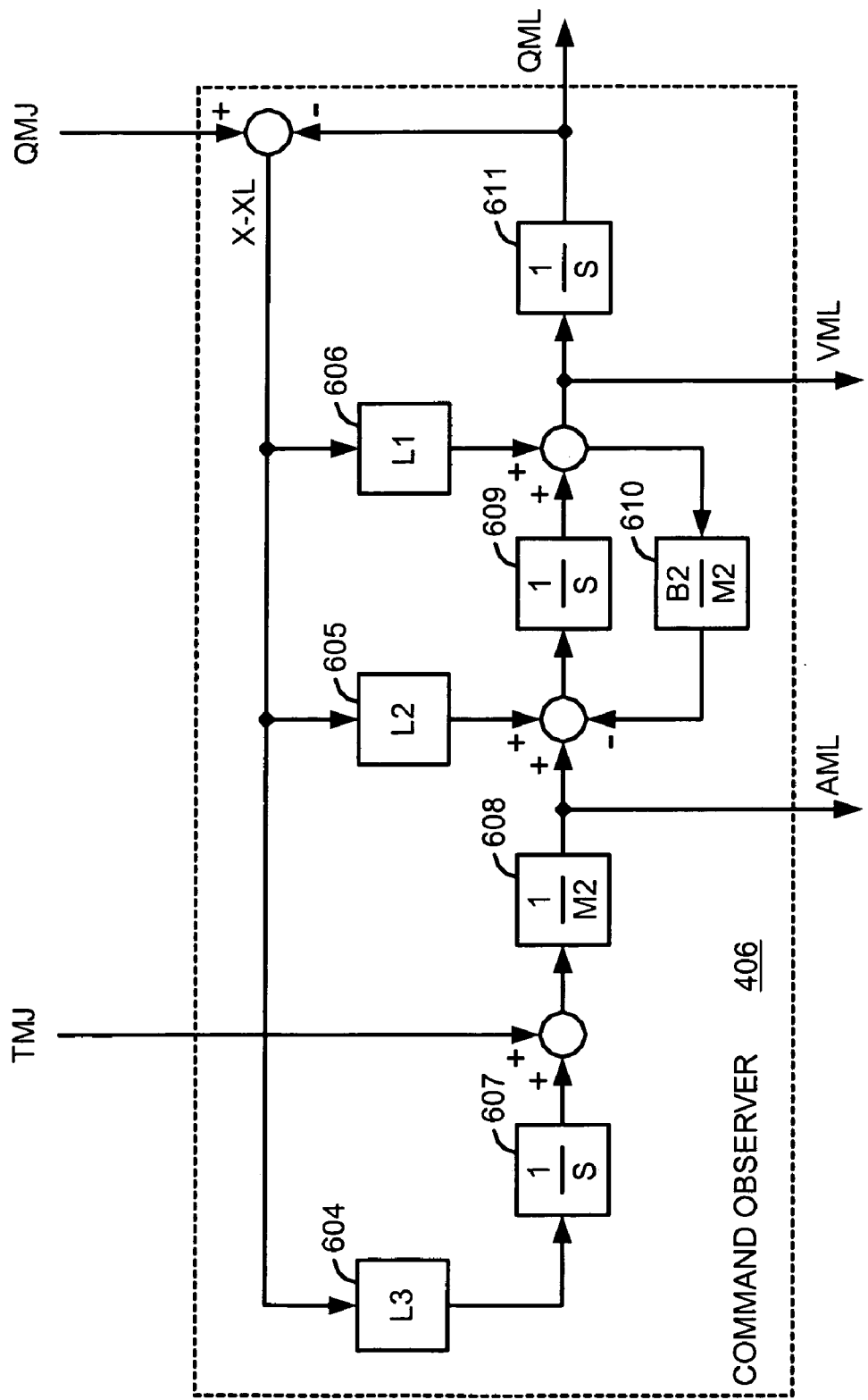
FIG. 6 illustrates a block diagram of a master command observer usable in a control system utilizing aspects of the present invention.

Also, to further enhance the accuracy and stability of the joint controller 400-1 and/or master/slave control system 300, a command observer 406 is preferably inserted so as to estimate joint position QML, velocity VML and acceleration AML commands using the joint position command QMJ and a torque feedback command TMJ. An example of the command observer 406 is shown configured as a disturbance observer structure in FIG. 6, wherein the parameters B2 and M2 come from a rigid model of the master dynamics, and the parameters L1, L2 and L3 are selected empirically through simulation and/or system calibration to provide good observer dynamics and accuracy (and may not necessarily be the same values as their counterparts in FIG. 5 even though they have the same parameter names). Note that the outputs of the command observer 406 are provided as negative values to the master controller 407 along with the outputs of the inverse filter 405, so that differences between corresponding of the inverse filtered, estimated joint positions QL, velocities VL and accelerations AL, and estimated joint position QML, velocity VML and acceleration AML commands may be calculated and used by the master controller 407 in generating the feedback torque TMJ. The master controller 407 in this case is preferably identical in construction as the slave controller 402.

Both the observers 404 and 406 may be based on joint models including one or more resonances. Additional details on such observers are described, for example, in commonly-owned U.S. application Ser. No. 11/479,144 "Control System for Reducing Internally Generated Frictional and Inertial Resistance to Manual Positioning of a Surgical Manipulator," filed Jun. 30, 2006, which is incorporated herein by this reference.

Although the various aspects of the present invention have been described with respect to a preferred embodiment, it will be understood that the invention is entitled to full protection within the full scope of the appended claims.

We claim:

1. A robotic surgical system comprising:
    a surgical instrument;
    a robotic arm assembly holding the surgical instrument;
    a master manipulator; and
    a controller configured to control movement of the surgical instrument in response to user operation of the master manipulator in such a manner that vibrations experienced at a tip of the surgical instrument are reduced by filtering an output of the master manipulator that may induce the vibrations while at least partially compensating in a feedback path to the master manipulator for delay induced by such filtering so as to enhance stability of such control.

2. The robotic surgical system according to claim 1, wherein the controller includes a control system to control movement of the robotic arm assembly in response to the user operation of the master manipulator, wherein the control system includes a filter for filtering the vibrations, and an inverse filter to at least partially compensate for delay caused by the filter in the control system.

3. The robotic surgical system according to claim 2, wherein the filter is characterized by attenuating high frequency signals above a cut-off frequency more than low frequency signals below the cut-off frequency.

4. The robotic surgical system according to claim 2, wherein the filter is further characterized by attenuating a resonant frequency signal caused by resonance of a mechanical structure supporting the robotic arm assembly so as to resemble a notch filter.

5. The robotic surgical system according to claim 2, wherein the filter is further characterized by attenuating a resonant frequency signal caused by resonance of the robotic arm assembly so as to resemble a notch filter.

6. The robotic surgical system according to claim 2, wherein the filter is implemented in a forward path of the control system from the master manipulator to the robotic arm assembly and the inverse filter is implemented in a feedback path of the control system from the robotic arm assembly to the master manipulator.

7. The robotic surgical system according to claim 2, wherein the filter is implemented such that the filter has an equal number of dominant poles and zeroes.

8. The robotic surgical system according to claim 2, wherein the filter is implemented such that the dominant poles of the filter are real and the dominant zeroes of the filter are complex.

9. The robotic surgical system according to claim 2, wherein the filter is implemented such that the dominant poles of the filter are less in magnitude than a resonant frequency of a mechanical structure associated with the robotic arm assembly.

10. The robotic surgical system according to claim 2, wherein an input of the filter includes at least one of a commanded position, commanded velocity, and commanded acceleration.

11. The robotic surgical system according to claim 10, wherein an output of the filter includes a filtered value for the commanded position, and a filtered value for the commanded velocity.

12. The robotic surgical system according to claim 11, wherein the output of the filter further includes a filtered value for the commanded acceleration.

13. The robotic surgical system according to claim 11, wherein the filter is digitally implemented as a state space balanced realization of the filter.

14. The robotic surgical system according to claim 11, wherein the commanded position is a position of a joint in the robotic arm assembly.

15. The robotic surgical system according to claim 2, wherein the control system further comprises a slave joint observer having: inputs including a sensed slave joint position of a slave joint in the robotic arm assembly, and a motor drive command for driving a slave joint motor adapted to move the slave joint; and outputs including at least estimated values for a position of the slave joint and a velocity of the slave joint.

16. The robotic surgical system according to claim 15, wherein the outputs of the slave joint observer further includes an estimated value for an acceleration of the slave joint.

17. The robotic surgical system according to claim 15, wherein the slave joint observer has a disturbance observer structure and the outputs of the slave joint observer further includes an estimated value for an external load being applied to the slave joint motor.

18. The robotic surgical system according to claim 15, wherein the motor drive command is generated by using at least one of the differences between corresponding of the filtered values for the commanded joint position and commanded joint velocity, and estimated values for the slave joint position and velocity.

19. The robotic surgical system according to claim 15, wherein part of the motor drive command is generated by using at least one of the filtered values for the commanded position, velocity, and acceleration.

20. The robotic surgical system according to claim 2, further comprising a master command observer having: inputs including a commanded joint position and a master motor drive feedback value; and outputs including estimated values for the commanded position and velocity.

21. The robotic surgical system according to claim 20, wherein the master command observer outputs further including an estimated value for the command acceleration.

22. The robotic surgical system according to claim 21, wherein the master command observer has a disturbance observer structure and the outputs of the master command observer further includes an estimated value for an external load applied to the master manipulator.

23. The robotic surgical system according to claim 2, wherein the inverse filter receives at least one of an estimated slave joint position, velocity and acceleration, and generates a filtered value for the at least one of the estimated slave position, velocity and acceleration.

24. The robotic surgical system according to claim 23, wherein the master motor drive feedback value is generated by using at least one of the differences between corresponding of the estimated values for the commanded position, velocity and acceleration, and outputs of the inverse filter.

25. The robotic surgical system according to claim 24, wherein part of the master motor drive command is generated by using at least one of the filtered values for the commanded position, velocity and acceleration.

* * * * *